United States Patent
Stern et al.

(10) Patent No.: US 8,043,271 B2
(45) Date of Patent: Oct. 25, 2011

(54) APPARATUS FOR TRANSPORTATION OF OXYGEN TO IMPLANTED CELLS

(75) Inventors: Yaki Stern, Shoham (IL); Uriel Barkai, MP Hof-Carmel (IL); Avi Rotem, Petach Tikva (IL); Meir Reingewirtz, Ramat Hashron (IL)

(73) Assignee: Beta 02 Technologies Ltd., Petach Tikva (IL)

( * ) Notice: Subject to any disclaimer, the term of this patent is extended or adjusted under 35 U.S.C. 154(b) by 0 days.

(21) Appl. No.: 12/315,102

(22) Filed: Nov. 26, 2008

(65) Prior Publication Data
US 2010/0130916 A1    May 27, 2010

(51) Int. Cl.
*A61M 37/00* (2006.01)
(52) U.S. Cl. .................. 604/288.01; 604/23
(58) Field of Classification Search .......... 604/23, 604/890.1–891.1, 175, 288.01, 288.02, 288.04
See application file for complete search history.

(56) References Cited

U.S. PATENT DOCUMENTS

| | | |
|---|---|---|
| 2,564,977 A | 8/1951 | Hu |
| 4,352,883 A | 10/1982 | Lim |
| 4,402,694 A | 9/1983 | Ash et al. |
| 4,631,053 A | 12/1986 | Taheri et al. |
| 4,721,677 A | 1/1988 | Clark, Jr. |
| 4,801,291 A | 1/1989 | Loori |
| 5,011,472 A | 4/1991 | Aebischer et al. |
| 5,029,579 A | 7/1991 | Trammell |
| 5,101,814 A | 4/1992 | Palti |
| 5,116,494 A | 5/1992 | Chick et al. |
| 5,262,055 A * | 11/1993 | Bae et al. ............. 210/645 |
| 5,336,209 A | 8/1994 | Porzilli |
| 5,381,075 A | 1/1995 | Jordan |
| 5,407,685 A | 4/1995 | Malchesky et al. |
| 5,427,935 A | 6/1995 | Wang et al. |
| 5,443,508 A | 8/1995 | Giampapa |
| 5,529,066 A | 6/1996 | Palti |
| 5,578,022 A | 11/1996 | Scherson et al. |
| 5,614,378 A | 3/1997 | Yang et al. |
| 5,662,625 A | 9/1997 | Westwood |
| 5,702,444 A | 12/1997 | Struthers et al. |
| 5,713,888 A | 2/1998 | Neuenfeldt et al. |

(Continued)

FOREIGN PATENT DOCUMENTS

GB    2024012    1/1980

(Continued)

OTHER PUBLICATIONS

Francis-Floyd, Ruth; Dissolved oxygen for fish production; Feb. 2003 (at the latest, see note at bottom), University of Florida; http://edis.ifas.ufl.edu/fa002.*

(Continued)

*Primary Examiner* — Theodore Stigell
*Assistant Examiner* — Bradley Osinski
(74) *Attorney, Agent, or Firm* — Abelman, Frayne & Schwab (57) ABSTRACT

Apparatus is provided which includes a housing, configured for insertion into a body of a subject. The apparatus includes functional cells coupled to the housing and a source of oxygen configured to supply oxygen to the functional cells. The apparatus further includes an oxygen delivery interface configured to receive oxygen from the source of oxygen, and to facilitate passage of the oxygen to the functional cells, while the housing is disposed within the body of the subject. Other embodiments are also described.

27 Claims, 5 Drawing Sheets

U.S. PATENT DOCUMENTS

| | | | |
|---|---|---|---|
| 5,741,334 | A | 4/1998 | Mullon et al. |
| 5,788,682 | A | 8/1998 | Maget |
| 5,792,090 | A | 8/1998 | Ladin |
| 5,834,005 | A | 11/1998 | Usala |
| 5,855,570 | A | 1/1999 | Scherson et al. |
| 5,855,613 | A | 1/1999 | Antanavich et al. |
| 5,879,709 | A | 3/1999 | Soon-Shiong et al. |
| 5,902,745 | A | 5/1999 | Butler et al. |
| 5,912,005 | A | 6/1999 | Lanza et al. |
| 6,000,403 | A | 12/1999 | Cantwell |
| 6,091,974 | A | 7/2000 | Palti |
| 6,148,232 | A | 11/2000 | Avrahami |
| 6,179,804 | B1 | 1/2001 | Satterfield |
| 6,268,161 | B1 | 7/2001 | Han et al. |
| 6,368,592 | B1 | 4/2002 | Colton et al. |
| 6,372,244 | B1 | 4/2002 | Antanavich et al. |
| 6,383,478 | B1 | 5/2002 | Prokop et al. |
| 6,630,154 | B1 | 10/2003 | Fraker et al. |
| 6,767,342 | B1 | 7/2004 | Cantwell |
| 6,960,351 | B2 | 11/2005 | Dionne et al. |
| 2003/0050622 | A1 | 3/2003 | Humes et al. |
| 2003/0087427 | A1 | 5/2003 | Colton et al. |
| 2003/0113302 | A1 | 6/2003 | Revazova et al. |
| 2004/0109302 | A1 | 6/2004 | Yoneda et al. |
| 2004/0133188 | A1* | 7/2004 | Vardi et al. ............ 604/891.1 |
| 2005/0025680 | A1 | 2/2005 | Monzyk et al. |
| 2005/0136092 | A1 | 6/2005 | Rotem et al. |
| 2006/0024276 | A1 | 2/2006 | Ricordi |
| 2007/0190038 | A1* | 8/2007 | Suzuki ..................... 424/93.7 |
| 2008/0086042 | A1 | 4/2008 | Brister et al. |
| 2009/0012502 | A1 | 1/2009 | Rotem et al. |

FOREIGN PATENT DOCUMENTS

| | | |
|---|---|---|
| WO | WO 90/15526 | 12/1990 |
| WO | WO 92/19195 | 11/1992 |
| WO | WO 94/20076 | 9/1994 |
| WO | WO 00/78920 | 12/2000 |
| WO | WO 01/50983 | 7/2001 |
| WO | WO 03/011445 | 2/2003 |
| WO | WO 2006/059322 | 6/2006 |
| WO | WO 2007/138590 | 3/2007 |
| WO | WO 2009/031154 | 3/2009 |

OTHER PUBLICATIONS

Wu H et al., "In-situ electrochemical oxygen generation with an immunoisolation device", Ann N Y Acad Sci 875:105-25 (1999).

L. Leheninger, Biochemistry, Worth Publishers, Inc. 1978, Chapter 14, pp. 363-364.

Smith AJ, "Acetate assimilation by nitrobacter agilis in relation to its 'obligate autotrophy' ", Journal of Bacteriology 95:844 (1968).

Klueth, et al., "Enhancement of implantable glucose sensor function in vivo using gene transfer-induced neovascularization", Biomaterials, vol. 26, No. 10, Apr. 2005. (an abstract).

Silva AI et al., "An overview on the development of a bio-artificial pancreas as a treatment of insulin- dependent diabetes mellitus," Med Res Rev 26 (2) : 181-222 (2006).

Faithful, N. S. Anaesthesia, 42, pp. 234-242 (1987).

Lacy PE et al., "Maintenance of normoglycemia in diabetic mice by subcutaneous xenografts of encapsulated islets," Science 1782-4 (1991).

Kaisers U et al., "Liquid ventilation," British Journal of Anaesthesia 91 (1) : 143-151 (2003).

Lorch H et al., "Central venous access ports placed by interventional radiologists: experience with 125 consecutive patients", Journal CardioVascular and interventional radiology, pp. 180-184, Issue vol. 24, No. 3 (2001).

Waschke KF, et al., "Modified haemolglobins and perfluorocarbons" (Current opinion in Anaesthesiology. 12(2):195-202 (1999).

Stagner, et al., "The Pancreas as an Islet Transplantation Site", Sep. 1, 2007, Journal of the Pancreas, vol. 8, No. 5, pp. 628-636.

An International Search Report and A Written opinion, both dated Jan. 25, 2010, which issued during the prosecution of Applicant's PCT/IL09/00905.

An Office Action dated Jun. 22, 2010, which issued during the prosecution of Applicant's U.S. Appl. No. 10/466,069.

An International Search Report and a Written opinion, both dated Jun. 9, 2010, which issued during the prosecution of Applicant's PCT/IL09/01114.

An office Action dated Jan. 7, 2011, which issued during the prosecution of Applicant's U.S. Appl. No. 11/001,556.

An Interview Summary dated Feb. 28, 2011, which issued during the prosecution of Applicant's U.S. Appl. No. 11/001,556.

An office Action dated May 31, 2011, which issued during the prosecution of Applicant's Japanese Patent Application No. 2007-544006.

An International Preliminary Report on Patentability, dated May 31, 2011, which issued during the prosecution of Applicant's PCT/IL2009/001114.

* cited by examiner

APPARATUS FOR TRANSPORTATION OF OXYGEN TO IMPLANTED CELLS

CROSS-REFERENCES TO RELATED APPLICATIONS

The present application is related to:

U.S. Provisional Patent Application 60/861,592, filed Nov. 28, 2006, entitled, "Oxygen supply for cell transplant and vascularization";

PCT Patent Application PCT/IL07/001471, filed Nov. 28, 2007, entitled, "Oxygen supply for cell transplant and vascularization";

U.S. Provisional Patent Application 60/993,052, filed Sep. 7, 2007, entitled, "Air gap for supporting cells";

U.S. patent application Ser. No. 12/064,946, filed Feb. 26, 2008, entitled, "Oxygen supply for cell transplant and vascularization";

PCT Patent Application PCT/IL08/001204, filed Sep. 7, 2008, entitled, "Air gap for supporting cells"; and U.S. Provisional Patent Application 61/192,412, filed Sep. 17, 2008, entitled, "Optimization of alginate encapsulation of islets for transplantation."

All of these applications are incorporated herein by reference.

FIELD OF THE INVENTION

The present invention relates generally to implantable medical devices. Specifically, the present invention relates to an implantable device to provide oxygen to transplanted cells, e.g., cells in transplanted pancreatic islets.

BACKGROUND OF THE INVENTION

Oxygen is vital to all physiological processes. An insufficient supply of oxygen to implanted cells often leads to cell injury or death. Oxygen provision is a vital component in sustaining transplanted cells.

In healthy individuals, insulin release is regulated so as to maintain blood glucose levels in the range of about 70 to 110 milligrams per deciliter. In diabetics, insulin is either not produced at all (Type I diabetes), or the body cells do not properly respond to the insulin that is produced (Type II diabetes). The result is elevated blood glucose levels.

The success of many cellular transplants is compromised not only due to graft-host rejections, but also on account of ischemic conditions generated by insufficient oxygen supply to the transplant. Following implantation of the cells, oxygen is provided to the implanted cells from the body tissue (mainly via diffusion), and in some cases, from vascular structures that form around the transplanted cells with the help of angiogenic factors, e.g., VEGF and bFGF. However, the natural diffusion rate is too low to provide the cells with a significant, necessary amount of oxygen.

PCT Publication WO 01/50983 to Vardi et al., and U.S. patent application Ser. No. 10/466,069 in the national phase thereof, which are incorporated herein by reference, describe an implantable device comprising a chamber for holding functional cells and an oxygen generator for providing oxygen to the functional cells. In one embodiment, the oxygen generator is described as comprising photosynthetic cells that convert carbon dioxide to oxygen when illuminated. In another embodiment, the oxygen generator is described as comprising electrodes that produce oxygen by electrolysis.

US Patent Application Publication 2005/0136092 to Rotem, which is incorporated herein by reference, describes apparatus including a chamber, which is adapted to be implanted in a body of an individual, the chamber including functional cells and chlorophyll-containing elements comprising chlorophyll of an obligate photoautotroph. Typically, the chlorophyll-containing elements include intact photosynthetic cells and/or isolated chloroplasts. The chlorophyll-containing elements provide oxygen to the functional cells and/or consume carbon dioxide produced by the functional cells. The chamber has one or more walls that are adapted to be permeable to nutrients and substances produced or secreted by the cells. The walls also typically immunoisolate the cells from constituents of the body. The chamber is adapted to be implanted under skin of the subject, or in the peritoneum. The apparatus further comprises a light source that is adapted to provide light to the chlorophyll-containing elements. The chamber may comprise an oxygen sensor that detects an oxygen concentration in a vicinity of the functional cells, and/or in a vicinity of the chlorophyll-containing elements. Providing the light in the series of pulses generally reduces power consumption of the apparatus, and/or provides control of the quantity of oxygen produced by the chlorophyll-containing elements, and/or provides control of the quantity of carbon dioxide consumed by the chlorophyll-containing elements. In some embodiments of the invention, the chamber comprises an oxygen reservoir, which typically comprises a material that stores and releases oxygen, such as responsively to an oxygen concentration in a vicinity of the reservoir. The oxygen reservoir typically stores oxygen produced by the chlorophyll-containing elements that is in excess of the current needs of the functional cells, and releases the stored oxygen if insufficient oxygen is later generated by the chlorophyll-containing elements.

PCT Publication WO 06/059322 to Evron et al., describes apparatus including a chamber which is adapted to be implanted in a body of an individual. The chamber includes functional cells and chlorophyll-containing elements comprising chlorophyll of an obligate photoautotroph. Other embodiments are also described.

U.S. Pat. No. 5,713,888 to Neuenfeldt et al., describes an implant assembly for a host tissue. The implant assembly comprises a pouch including wall means defining a chamber for holding a second member. The wall means includes an outer vascularizing membrane having a conformation that results in growth of vascular structures by the host tissue, close to an interface between the vascularizing membrane and host tissue. The assembly includes a second member that can be removably inserted in the chamber including an interior for receiving cells and wall means defining an immuno-isolating membrane that isolates the cells from the immune response of the host tissue.

U.S. Pat. No. 6,368,592 to Colton et al., describes techniques for supplying oxygen to cells in vitro or in vivo by generating oxygen with an oxygen generator that electrolyzes water to oxygen and hydrogen.

U.S. Pat. No. 6,960,351 to Dionne et al., describes an immunoisolatory vehicle for the implantation into an individual of cells which produce a needed product or provide a needed metabolic function. The vehicle is comprised of a core region containing isolated cells and materials sufficient to maintain the cells, and a permselective, biocompatible, peripheral region free of the isolated cells, which immunoisolates the core yet provides for the delivery of the secreted product or metabolic function to the individual. The vehicle is described as being particularly well-suited to delivery of insulin from immunoisolated islets of Langerhans, and as being used advantageously for delivery of high molecular weight products, such as products larger than IgG.

The following patents and patent applications may be of interest:

PCT Publication WO 07/138590 to Gross
U.S. Pat. No. 2,564,977 to Hu
U.S. Pat. No. 4,721,677 to Clark, Jr. et al.
U.S. Pat. No. 5,614,378 to Yang et al.
U.S. Pat. No. 6,268,161 to Han, et al.
U.S. Pat. No. 6,383,478 to Prokop, et al.
U.S. Pat. No. 6,630,154 to Fraker, et al.
US Patent Application Publication 2003/0113302 to Revazova et al.
US Patent Application Publication 2005/0025680 to Monzyk et al.
US Patent Application Publication 2006/0024276 to Ricordi et al.

The following articles may be of interest:

Kaisers U et al., "Liquid ventilation," British Journal of Anaesthesia 91(1):143-151 (2003)

Lacy P E et al., "Maintenance of normoglycemia in diabetic mice by subcutaneous xenografts of encapsulated islets," Science 1782-4 (1991)

Lorch H et al., "Central Venous Access Ports Placed by Interventional Radiologists: Experience with 125 Consecutive Patients," Journal CardioVascular and Interventional Radiology, Pages 180-184, Issue Volume 24, Number 3 (2001)

Silva A I et al., "An overview on the development of a bio-artificial pancreas as a treatment of insulin-dependent diabetes mellitus," Med Res Rev 26(2):181-222 (2006)

Waschke K F and Frietsch T, "Modified haemoglobins and perfluorocarbons" (Current Opinion in Anaesthesiology. 12(2):195-202 (1999)

SUMMARY OF THE INVENTION

In some embodiments of the present invention, apparatus comprises a housing for containing transplanted cells that is designated for subcutaneous implantation into the body of a subject. The transplanted cells typically comprise functional cells, e.g., cells disposed in pancreatic islet of Langerhans cells, and in this case are typically in islets. The functional cells are typically disposed in a layer of liquid or gel. The housing comprises an oxygen delivery interface (e.g., a penetrable surface, one or more valves, or one or more tubes) that facilitates the transfer of oxygen to the cells. The apparatus comprises a source of oxygen, or an oxygen supply (e.g., a vessel comprising air, another mixture of gases, or pure oxygen), that is connectable to the housing via the interface. At regular intervals, e.g., every few hours or every few weeks, typically, at least once a week, the subject connects the source of oxygen to the interface, and the source of oxygen supplies a limited amount of oxygen to the housing.

In some embodiments, the source of oxygen comprises a container comprising a plurality of gases including oxygen. The gases are disposed in the container at a pressure of 1 atm or higher. Typically, the source of oxygen comprises around 5% carbon dioxide in order to maintain a balance of concentrations of carbon dioxide inside the housing and outside the housing. For some applications, the source of oxygen comprises a liquid comprising oxygen carriers (e.g., hemoglobin-based oxygen carriers such as chemically-modified hemoglobin, or "microbubbles" which comprise fluorocarbons such as dodecafluoropentane, perfluorodecalin, or other perfluorochemicals) that are loaded with oxygen prior to the injection of the carriers into the housing.

Typically, the housing comprises an oxygen reservoir, which functions as a conduit for oxygen diffusion as well as a reservoir for storing excess oxygen that is supplied to the housing by the source of oxygen. In some embodiments, the oxygen reservoir comprises a gas reservoir, which is an area of gas in the housing comprising oxygen and carbon dioxide. In some embodiments, the oxygen reservoir comprises liquid-based oxygen carriers. In such an embodiment, the oxygen carriers function to store, or carry, oxygen when in excess, and release the oxygen upon a need therefor.

For some applications, the housing comprises a plurality of projections which project radially from a center of the housing. The oxygen carriers are typically stored within the projections, which provide increased surface area for absorbing oxygen from vasculature surrounding the housing. The oxygen absorbed via the projections is stored in the housing by the oxygen carriers.

Typically, oxygen is supplied to the housing in a volume and concentration in accordance with the, size of the housing and with the number of functional cells disposed therein. Additionally, the amount of oxygen delivered to the housing depends on the composition of the oxygen carriers injected into the housing. That is, a given volume of fluid comprising preloaded oxygen carriers will sustain the functional cells in the housing for a longer period than will the same volume of fluid comprising free oxygen. In general, the oxygen delivery interface facilitates the provision, on a consistent basis, of oxygen to the functional cells in a volume and concentration sufficient to meet the oxygen consumption rate of the functional cells over a given period of time, e.g., between 12 hours and 2 weeks.

In some embodiments, the oxygen delivery interface comprises a surface of the housing that comprises a material that is penetrable, e.g., rubber, silicone, or plastic, and provides access to an interior of the housing following penetration of the surface. In such an embodiment, the source of oxygen is coupled to a device, e.g., a needle, which transcutaneously accesses the oxygen delivery interface of the housing. For embodiments in which the source of oxygen is coupled to a needle, the needle punctures the skin of the subject and subsequently the surface of the housing.

Fluid having a low oxygen content disposed within the housing is removed therefrom in conjunction with the supplying to the housing of the fluid having a high oxygen content. (It is noted that "fluid" includes within its scope both liquids and gases.) In some embodiments, the needle comprises a double-chambered needle having an input chamber and an output chamber. Fluid having a high oxygen content is actively injected into the housing via the input chamber (e.g., by the user operating a normal syringe, or by an electrical mechanism). In conjunction with the injecting, and in response to the pressure introduced within the housing due to the injection of the fluid having a high oxygen content, fluid disposed within the housing is passively withdrawn therefrom through the outlet chamber.

In some embodiments, the needle comprises a single-chambered needle, and the source of oxygen comprises a syringe that is coupled to a pump. Prior to the supplying of the oxygen to the cells, the syringe is coupled to the needle, the needle punctures the housing, and the pump draws a portion of fluid having a low oxygen content from within the housing through the syringe. A portion of fluid having a high oxygen content within the syringe is then injected into the housing. In such an embodiment, the pump facilitates cycling of (a) active drawing of fluid from within the housing, and (b) the replenishing of the fluid. In an embodiment, the user performs this cycling, without a pump.

In some embodiments, the housing is in fluid communication with one or more ports which each comprise a penetrable surface, which facilitates access to the interior of the housing by a needle. The ports are in contact with the subcutaneous tissue of the subject. In some embodiments, the ports are directly coupled to a surface of the housing that is in contact with subcutaneous tissue. Alternatively, the ports are disposed remotely with respect to the housing and are coupled thereto via respective tubes.

In some embodiments, the housing is in fluid communication with a fluid inlet tube and a fluid outlet tube having respective first ends thereof that are disposed within the housing. The respective second ends of the input and output tubes are disposed outside the body of the subject. Typically, the end of the input tube that is disposed outside the body of the subject serves as the oxygen delivery interface. Oxygen from the source of oxygen is injected via the input tube and into the housing in order to replenish the fluid and increase the oxygen concentration in the housing. In conjunction with the active injecting of the fluid into the housing, fluid disposed within the housing passively exits the housing via the output tube or is actively drawn from the housing by coupling a source of suction to the outlet tube.

In some embodiments, the housing is flexible and is implanted in a vicinity of a ribcage of the subject. In such an embodiment, the oxygen-containing fluid is actively, continuously transported within the housing in response to movement of the flexible housing occurring responsively to the natural movements of the ribcage.

In some embodiments of the present invention, apparatus comprises a housing containing the functional cells is implanted subcutaneously in a vicinity of a trachea of the subject. The housing is indirectly coupled to the trachea by a fluid transport tube having a first end disposed within the housing, and a second end disposed adjacent to the trachea. A "T"-shaped tracheal mount couples the fluid transport tube to the trachea and serves as the oxygen delivery interface by creating a conduit for supplying air to the housing from the trachea. The housing comprises a depressible upper surface that is in contact with the subcutaneous tissue of the subject. The depressible surface is depressible by the subject who pushes on a portion of his or her skin that is disposed above the depressible surface. By pushing the depressible surface, air is forced out of the housing, through the fluid transport tube, and into the trachea of the subject. The depressible surface is resilient and returns to its original state following the pushing of the surface by the subject. Consequently, reduced pressure is generated in the housing, which draws air from the trachea into the housing, via the fluid transport tube.

There is therefore provided, in accordance with an embodiment of the present invention, apparatus, including:

a housing, configured for implantation in a body of a subject;

functional cells, coupled to the housing;

a source of oxygen configured to supply oxygen to the functional cells; and an oxygen delivery interface coupled to the housing, configured to receive oxygen from the source of oxygen, and to facilitate passage of the oxygen to the functional cells, while the housing is disposed within the body of the subject.

In an embodiment, the functional cells include cells disposed in pancreatic islets.

In an embodiment, the source of oxygen includes a plurality of gases.

In an embodiment, the source of oxygen includes oxygen carriers preloaded with oxygen.

In an embodiment, the oxygen delivery interface is reversibly couplable to the source of oxygen.

In an embodiment, the housing is configured to provide oxygen-containing gas in a volume sufficient to sustain the functional cells for a period of between 12 hours and 2 weeks.

In an embodiment, the housing is shaped to provide a plurality of projections which project into tissue of the subject, the projections being configured to absorb oxygen from vasculature of the subject.

In an embodiment, the functional cells are disposed in at least one layer of hydrogel configured to immunoisolate the cells from the body of the subject.

In an embodiment, the housing is shaped to provide an oxygen reservoir layer, and the functional cells are disposed in at least first and second layers of hydrogel, the first and second layers being disposed on either side of the oxygen reservoir layer.

In an embodiment, the oxygen reservoir layer has a longest dimension that is longer than a longest dimension of either of the first and second layers of the functional cells, and the oxygen reservoir layer provides surface area for absorbing oxygen from surrounding vasculature of the subject.

In an embodiment, the oxygen reservoir layer is shaped to provide a series of channels which facilitate directed transport of fluids within the oxygen reservoir layer.

In an embodiment, the oxygen reservoir layer includes at least one valve configured to facilitate directed transport of fluids within the oxygen reservoir layer.

In an embodiment, the housing is configured to be implanted in a vicinity of a ribcage of the subject, and the housing is configured to circulate the oxygen in the reservoir layer in response to movements of the housing responsively to movements of the ribcage of the subject.

In an embodiment, the oxygen reservoir layer includes a hydrogel shaped to define a channel configured to facilitate directed transport of oxygen within the reservoir layer.

In an embodiment, the oxygen reservoir layer includes the oxygen delivery interface and is couplable to and receives oxygen from the source of oxygen.

In an embodiment, the oxygen delivery interface includes an interface between the reservoir layer and one of the first and second layers of cells.

In an embodiment, the oxygen reservoir layer includes a gas.

In an embodiment, the oxygen reservoir layer includes oxygen carriers.

In an embodiment:

during a first time, the interface is configured to facilitate:

coupling of the source of oxygen to the housing, supplying of oxygen from the source of oxygen to the cells coupled to the housing, and decoupling of the source of oxygen from the interface following the supplying of oxygen, and at a second time, the interface is configured to facilitate:

coupling of the source of oxygen to the housing, supplying of oxygen from the source of oxygen to the cells coupled to the housing, and decoupling of the source of oxygen from the interface following the supplying of oxygen.

In an embodiment:

the interface includes a penetrable surface, the apparatus further includes a needle configured for transcutaneously penetrating the surface with the needle, the housing is indirectly couplable to the source of oxygen via the needle, and the needle facilitates supplying of oxygen to the cells from the source of oxygen.

In an embodiment, the housing is shaped to define an upper surface, and the penetrable surface includes the upper surface of the housing.

In an embodiment, the apparatus includes at least one oxygen-delivery port having an upper surface thereof and a tube coupled at a first end thereof to the port and at a second end thereof to the housing, wherein the upper surface of the port includes the penetrable surface that is penetrable by the needle.

In an embodiment, the port is coupled to an upper surface of the housing.

In an embodiment, the port is disposed remotely from the housing.

In an embodiment:

the interface includes at least one fluid inlet tube in fluid communication with the housing, the housing is indirectly couplable to the source of oxygen via the fluid inlet tube, and the tube facilitates supplying of oxygen to the cells from the source of oxygen.

In an embodiment, the fluid inlet tube is configured to be disposed transcutaneously in the body of the subject.

In an embodiment, the housing is shaped to define an oxygen reservoir to store oxygen provided to the housing from the source of oxygen.

In an embodiment, the oxygen reservoir is configured to store fluid at a pressure of at least 1 atm.

In an embodiment, a volume of the reservoir is between 100 ml and 300 ml.

In an embodiment, the oxygen reservoir includes a gas.

In an embodiment, the oxygen reservoir includes oxygen carriers configured to absorb excess oxygen disposed in the oxygen reservoir.

In an embodiment, the apparatus includes a gas-permeable membrane disposed between the reservoir and the functional cells.

In an embodiment:

the oxygen delivery interface includes at least one fluid inlet tube in fluid communication with the housing, and a first end of the tube is reversibly couplable to the source of oxygen, in a manner that allows the source of oxygen to supply oxygen to the functional cells via the tube.

In an embodiment, the fluid inlet tube is configured to be disposed transcutaneously in the body of the subject.

In an embodiment, the apparatus includes a fluid outlet tube in communication with the housing, and the fluid outlet tube is configured to facilitate passage of fluid from within the housing to a site external to the housing.

In an embodiment, the fluid outlet tube is configured to be disposed transcutaneously in the body of the subject.

In an embodiment, the fluid outlet tube is configured to facilitate passive passage of the fluid from within the housing, in conjunction with the supplying of oxygen to the housing by the fluid inlet tube.

In an embodiment, the apparatus further includes a source of suction configured to facilitate active drawing of fluid from within the housing.

In an embodiment, the oxygen delivery interface includes a penetrable surface.

In an embodiment, the apparatus includes a needle having at least one chamber, the needle is couplable to the source of oxygen and is configured for transcutaneous penetration of the penetrable surface of the housing.

In an embodiment, the at least one chamber is configured to facilitate delivery of oxygen from the source of oxygen to the functional cells coupled to the housing.

In an embodiment:

the at least one chamber includes a first chamber and a second chamber, the first chamber is configured to facilitate delivery of oxygen from the source of oxygen to the functional cells coupled to the housing, and the second chamber is configured to facilitate passage of fluid from within the housing to outside the body of the subject.

In an embodiment, the second chamber is configured to facilitate passive passage of the fluid from within the housing, in conjunction with the supplying of oxygen to the housing by the first chamber.

There is additionally provided, in accordance with an embodiment of the present invention, a method for use with apparatus including an implantable housing including functional cells and an oxygen delivery interface, the method including:

at a first time:
coupling a source of oxygen to the interface;
supplying oxygen from the source of oxygen to the cells; and
decoupling the source of oxygen from the interface; and at a second time:
coupling the source of oxygen to the interface; supplying oxygen from the source of oxygen to the cells; and
decoupling the source of oxygen from the interface.

In an embodiment, the functional cells include cells disposed in pancreatic islets of Langerhans, and supplying oxygen from the source of oxygen to the cells includes supplying oxygen from the source of oxygen to the islets.

In an embodiment, the method includes facilitating passive passage of fluid from the housing in conjunction with the supplying of oxygen to the housing during the first and second times.

In an embodiment, the method includes actively drawing fluid from the housing in conjunction with the supplying of oxygen to the housing during the first and second times.

In an embodiment, the method includes regulating a rate of oxygen transport from the reservoir to the functional cells.

In an embodiment, regulating the rate of oxygen transport includes providing oxygen carriers in the reservoir which absorb excess oxygen in the reservoir and release the oxygen in a low oxygen environment.

There is further provided, in accordance with an embodiment of the present invention, apparatus, including:

a housing, configured for implantation in a body of a subject, the housing:
shaped to define an oxygen reservoir, and
including a flexible upper surface thereof;
functional cells, coupled to the hosing; and
a tube coupled to the housing, the tube having a first end thereof that is in fluid communication with the reservoir and a second end thereof configured to be in fluid communication with a trachea of the subject, the tube being configured to facilitate oxygen transport to the functional cells in response to a pushing force applied to the upper surface of the housing.

In an embodiment, the housing is configured to be disposed remotely from the trachea.

In an embodiment, the upper surface is configured to facilitate pumping of gas from the trachea into the housing.

In an embodiment, the upper surface, in response to the pushing force applied thereto, is configured to force air out of the reservoir and through the tube toward the trachea.

In an embodiment, following the pushing force applied to the upper surface, the upper surface is configured to reduce a pressure in the reservoir and draw air into the reservoir from the trachea via the tube.

In an embodiment, the functional cells are disposed in at least one layer of hydrogel configured to immunoisolate the cells from the body of the subject.

In an embodiment, the method further includes provided an oxygen reservoir layer, and the functional cells are disposed in first and second layers of hydrogel, the first and second layers being disposed on either side of the oxygen reservoir layer.

In an embodiment, the reservoir layer is configured to absorb oxygen from surrounding vasculature of the subject.

In an embodiment, the oxygen reservoir layer is in communication with the first end of the tube and receives oxygen from the trachea via the tube.

There is also provided, in accordance with an embodiment of the present invention a method, including:

subcutaneously implanting in a body of a subject, a housing shaped to define an oxygen reservoir and shaped to provide a flexible upper surface that is in contact with subcutaneous tissue of the subject;

implanting a first portion of a tube in a trachea of the subject, the tube having a second end in communication with the oxygen reservoir of the housing; and facilitating transport of oxygen from the trachea into the reservoir of the housing and toward the cells by applying a pushing force to the upper surface of the housing.

In an embodiment, applying the pushing force includes forcing the air out of the reservoir and into the trachea of the subject.

The present invention will be more fully understood from the following detailed description of embodiments thereof, taken together with the drawings, in which:

DETAILED DESCRIPTION OF THE EMBODIMENTS

Figures 1A, 1B:
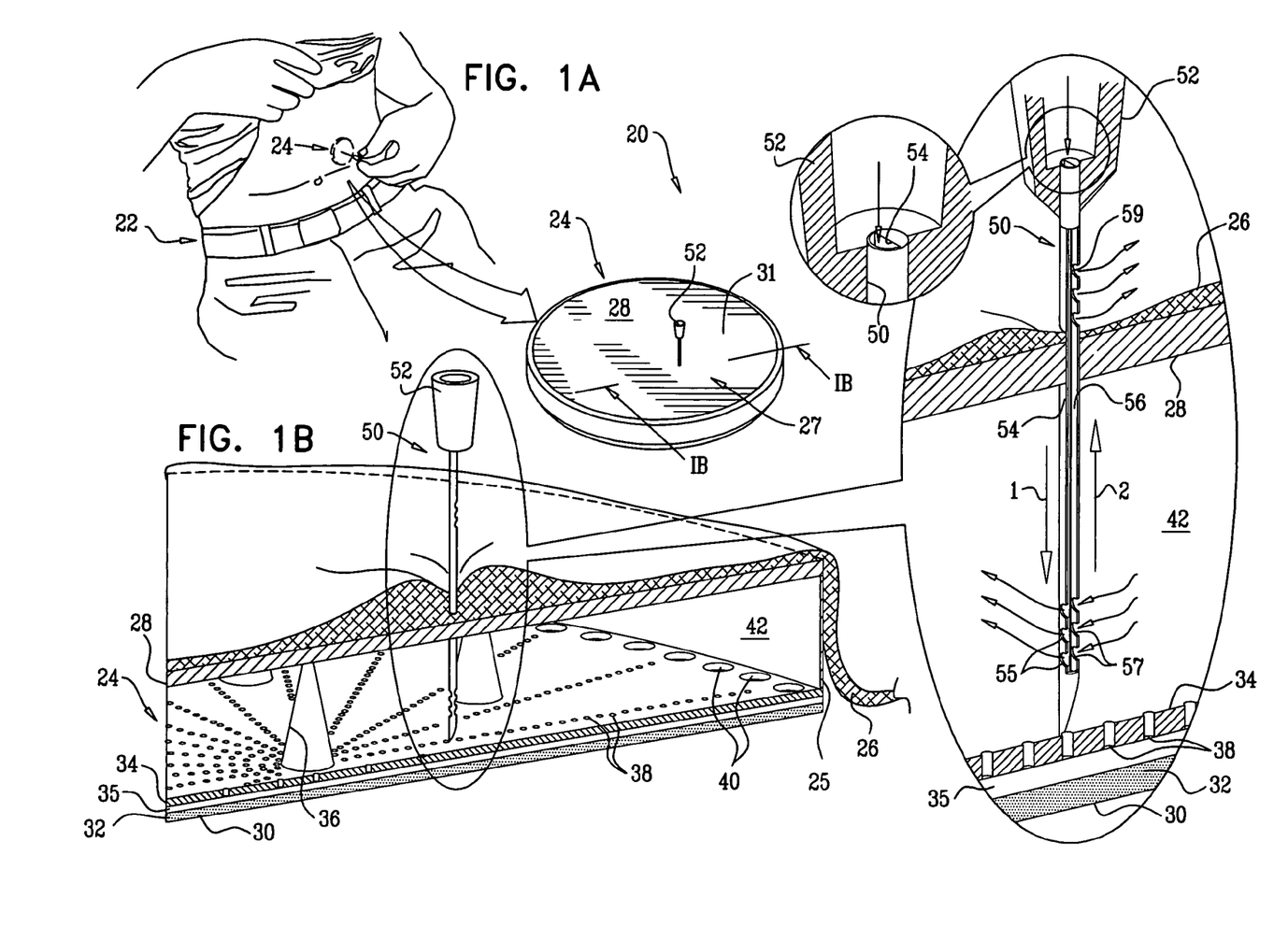
FIGS. 1A-B are schematic illustrations of a housing comprising a penetrable surface and housing functional cells, in accordance with an embodiment of the present invention.

Reference is now made to FIGS. 1A-B, which are schematic illustrations of a system 20 comprising a subcutaneously-implantable housing 24 containing a layer 32 of functional cells, e.g., disposed in transplanted pancreatic islets of Langerhans, in accordance with an embodiment of the present invention. Housing 24 comprises a scaffold 25, e.g., silicone or metal, which separates layer 32 of functional cells from a surface 28 comprising a penetrable material, e.g., rubber, silicone, or plastic. Typically an upper surface 31, i.e., the surface of housing 24 that is in contact with subcutaneous tissue of subject 22, comprises penetrable surface 28. Surface 28 serves as an oxygen delivery interface 27, which by being punctured facilitates access to housing 24 by a disposable needle 50. A source of oxygen (not shown), e.g., a vessel such as a syringe, comprising a source of fluid which comprises oxygen, is coupled to needle 50 and supplies via needle 50 fluid containing oxygen to the functional cells (e.g., in islets) that are disposed within housing 24. In some embodiments, the source of oxygen comprises air. Alternatively, the source of oxygen comprises pure oxygen.

Typically, layer 32 comprises between 40,000 and 400,000 islets, e.g., typically, 400,000 islets, which are evenly distributed in a single layer 32. As appropriate for a given application, the number of islets may also be outside of this range. In some embodiments, the islets are arranged in a manner in which every second row of islets in layer 32 is offset with respect to its neighboring row of islets (configuration shown in FIG. 2). Oxygen is typically supplied to the islets in layer 32 in a volume and concentration in which the partial pressure of oxygen in each islet is between 8 and 40 uM, or between 40 and 200 uM.

In some embodiments, the source of oxygen comprises a plurality of gases including oxygen. The gases are disposed in the container at a pressure of 1 atm or higher. Typically, the source of oxygen comprises around 5% carbon dioxide in order to maintain a balance of concentrations of carbon dioxide inside the housing and outside the housing. For some applications, the source of oxygen comprises a fluid comprising oxygen carriers (e.g., hemoglobin-based oxygen carriers such as chemically-modified hemoglobin, or "microbubbles" which comprise fluorocarbons such as dodecafluoropentane or perfluorodecalin) that are loaded with oxygen prior to the injection of the carriers into housing 24. The carriers facilitate the transport into housing 24 of a larger volume of compressed oxygen.

Typically, the functional cells of layer 32 are disposed in a layer of liquid or gel, such as alginate, agarose, or polyethylene glycol (PEG) and/or dispersed in a three-dimensional biodegradable or non-biodegradable fibrillar matrix. In some embodiments, layer 32 comprises an alginate slab which houses the functional cells and functions to immunoisolate the cells. This embodiment may be practiced in combination with techniques described in U.S. Provisional Patent Application 61/192,412 to Barkai et al., which is incorporated herein by reference.

Layer 32 has an interface 30 in contact with the body of a subject 22. Typically, insulin and/or other by-products of the functional cells are released to the body through interface 30. In some embodiments, interface 30 comprises a surface of the alginate slab. In some embodiments, interface 30 comprises a selectively-permeable membrane which immunoisolates the transplanted cells as well as facilitates transport of (a) molecules, e.g., insulin, from the cells to the body of subject 22, and (b) molecules, e.g., glucose, from the body of subject 22 to the cells in housing 24.

Scaffold 25 defines a space comprising an oxygen reservoir 42, typically having a volume of between 100 ml and 300 ml, e.g., between 150 ml and 200 ml. Oxygen reservoir 42 comprises foam, e.g., an open-cell silicone foam, or simply an air gap which functions as a gas reservoir within the device. Reservoir 42 functions as a conduit for oxygen diffusion to the functional cells, as well as a reservoir for storing excess oxygen that is supplied to the housing by the source of oxygen. Techniques described herein with respect to reservoir 42 may be practiced in combination with techniques described with respect to an air gap in PCT Patent Application PCT/IL08/001204 to Stern et al., which is incorporated herein by reference.

In some embodiments, the housing comprises the oxygen carriers. In such an embodiment, the oxygen carriers function to store, or carry, oxygen when in excess, and release the oxygen upon a need therefor.

Housing 24 is shown as being disc-shaped by way of illustration and not limitation. For example, housing 24 may be rectangular or any other suitable shape suitable for implantation under skin 26 of subject 22. In some embodiments, housing 24 is shaped to provide a plurality of projections which project radially from housing 24 and toward a vicinity of the body of subject 22 which includes vasculature. In such an embodiment, the projections function as oxygen delivery interface 27 by providing increased surface area of housing 24 for facilitating transport of oxygen from surrounding vasculature toward housing 24. For some applications, the projections of housing 24 contain the oxygen carriers, which store excess oxygen that has been absorbed into housing 24 by the projections.

At some time following implantation of housing 24 in the body of subject 22, housing 24 is primed with a suitable amount of oxygen-containing fluid. (The housing may have previously been filled with oxygen-containing fluid, as well.) Typically, the subject 22 transcutaneously punctures surface 28 of housing 24 using needle 50, and advances a distal tip of needle 50 through reservoir 42 and toward layer 32 of functional cells. Contact between layer 32 of cells and the distal tip of needle 50 is prevented by a substantially rigid separating layer 34 that is disposed above and protects layer 32 of functional cells. A plurality of vertical supports 36 are disposed between separating layer 34 and surface 28 of housing 24.

For some applications, separating layer 34 is shaped to define a plurality of channels 38 and 40 which facilitate bidirectional transport of oxygen (a) from reservoir 42 toward layer 32 of cells, and (b) carbon dioxide from layer 32 of cells toward reservoir 42. Alternatively, oxygen travels from reservoir 42 to layer 32 by other routes.

In an embodiment, housing 24 comprises a gas-permeable membrane 35, e.g., a Millipore membrane and/or a membrane comprising silicone, that is disposed between layer 32 of functional cells and separating layer 34. Gas-permeable membrane 35 facilitates the transport of gases to and from layer 32 of functional cells. Typically, membrane 35 has a width and a pore size which regulates a rate of transport of gases to and from layer 32.

An enlarged image of FIG. 1B shows a cross-sectional illustration of needle 50. Needle 50 comprises a double-chambered needle comprising a fluid inlet chamber 54 and a fluid outlet chamber 56. A proximal end of needle 50 is coupled to a luer connector 52 which facilitates the coupling of a vessel (e.g., a syringe) comprising oxygen-containing fluid. Luer connector 52 is in fluid communication with a proximal end of fluid inlet chamber 54. The fluid is actively expelled from the syringe through chamber 54 and exits chamber 54 via one or more perforations 55 at the distal end of needle 50, in order to enter reservoir 42 of housing 24.

When fluid comprising a high oxygen content is actively injected into reservoir 42 (i.e., in a direction as indicated by arrow 1), fluid disposed within reservoir 42 having a low oxygen content passively exits reservoir 42 through one or more perforations 57 in fluid outlet chamber 56. The fluid having a low oxygen content exits needle 50 by traveling in a direction as indicated by arrow 2, and through one or more perforations 59 at a proximal portion of chamber 56 that is disposed outside a surface of skin 26 of subject 22.

It is to be noted that needle 50 comprises three of each perforations 55, 57, and 59 by way of illustration and not limitation, and that needle 50 may be shaped to define any suitable number of perforations 55, 57, and 59.

It is to be noted that the plurality of perforations 55 of chamber 54 are disposed with respect to the plurality of perforations 57 of chamber 56, at substantially the same cross-sectional plane of needle 50 by way of illustration and not limitation. For example, perforations 55 may be disposed at a more proximal site of the intracorporeal portion of needle 50 while perforations 57 are disposed at a more distal site of the intracorporeal portion of needle 50.

Typically, fluid having a high oxygen content is injected into reservoir 42 in excess. In some embodiments, the excess oxygen is in the form of free gas. Alternatively, the excess oxygen is loaded onto oxygen carriers, as described hereinabove. Providing the oxygen in excess is done in order to ensure that sufficient oxygen-containing fluid remains within reservoir 42 following the passive transport of fluid through fluid outlet chamber 56 (which occurs in conjunction with the injecting).

Typically, oxygen is supplied to housing 24 in a volume and concentration in accordance with the size of housing 24 and with the amount of functional cells disposed therein. Additionally, the amount of oxygen delivered to housing 24 depends on the composition of the fluid injected into housing 24. That is, a given volume of fluid comprising preloaded oxygen carriers will sustain the functional cells in housing 24 for a longer period than will the same volume of fluid comprising free oxygen. In general, oxygen delivery interface 27 facilitates the provision, on a recurring basis, of oxygen to the functional cells in a volume and concentration sufficient to meet the oxygen consumption rate of the functional cells over a given period of time, e.g., between 12 hours and 2 weeks.

The following table depicts, by way of illustration and not limitation, the projected parameters relating to the source of oxygen with respect to the size of housing 24 comprising 400,000 islets in various distributions thereof within housing 24, in accordance with various embodiments of the present invention:

| Cell layer # | CTC (um) | ID | Diam. | K Alginate (mm 2/s) | Alginate slab thickness (um) | P Min (uM) | W (mm) |
|---|---|---|---|---|---|---|---|
| 1 | 155 | 4808 | 103 | 1.5E–03 | 250 | 180 | 91 |
| 1 | 165 | 4237 | 110 | 1.5E–03 | 250 | 161 | 52 |
| 1 | 175 | 3769 | 116 | 1.5E–03 | 250 | 145 | 36 |
| 1 | 175 | 3769 | 116 | 2.5E–03 | 250 | 108 | 23 |
| 1 | 175 | 3769 | 116 | 1.5E–03 | 200 | 125 | 28 |
| 1 | 185 | 3769 | 116 | 1.5E–03 | 200 | 90 | 20 |
| 1 | 185 | 3371 | 123 | 1.5E–03 | 250 | 133 | 27 |
| 2 | 265 | 3290 | 124 | 1.5E–03 | 350 | 176 | 56 | where:

Cell layer # is the number of cell layers (either one (as in FIG. 1B) or two (as in FIG. 7));

CTC is the center to center distance between the islets, i.e., the distance from the center of one islet to the center of a neighboring islet;

ID is islet density (islets/cm2);

Diam. is the diameter of each alginate slab (mm);

K Alginate is the permeation coefficient of oxygen in the alginate of the alginate slab (mm^2/s);

P min is the minimum partial pressure of oxygen in reservoir 42, such that the partial pressure of oxygen within each islet is between 8 and 200 uM, which is sufficient for sustaining functional islets. Typically, the oxygen in reservoir 42 may be depleted to a minimum of about 90 uM and subsequently restored to about 215 uM (corresponding to about 21% oxygen). It is to be noted that for some applications, the partial pressure may be restored to a value greater than 215 uM, e.g., reservoir 42 may contain 21%-50% or 50%-100% oxygen; and W is the thickness/width of reservoir 42.

Typically, housing 24 comprises a single layer 32 of functional cells disposed in a single, thin alginate slab having a high permeation coefficient. Typically, layer 32 of functional cells comprises 300,000-500,000 islets of Langerhans (e.g., around 400,000) having a density of between 3200 and 5000 islets/cm^2, e.g., 3700-4000 islets/cm^2.

In general, housing 24 has a diameter of between 100 mm and 150 mm, e.g., 125 mm, and a width of between 20 mm and 100 mm, e.g., 25 mm. Housing 24 is typically primed with air comprising 21% oxygen. Oxygen is typically supplied to housing 24 in a concentration between 30 and 500 uM, e.g., 57-215 uM. Housing 24 is configured to contain gases at a pressure of 1 atm or greater.

At regular intervals (e.g., at least once a week, typically, once a day), subject 22 reintroduces needle 50 within housing 24 via oxygen delivery interface 27. At such intervals, a source of oxygen (e.g., a syringe or pre-filled cartridge) is connected to needle 50 and supplies oxygen-containing fluid to the islets in housing 24.

It is to be noted that needle 50 is shown as comprising a double-chambered needle by way of illustration and not limitation. For example, needle 50 may comprise a single-chambered needle. In such an embodiment, the source of oxygen may be coupled to a pump which facilitates cycling between (1) gradually actively injecting a portion of fluid having a high oxygen content from the source of oxygen and into housing 24, and (2) gradually actively drawing (or passively allowing) fluid having a low oxygen content out of housing 24. For some applications, the user may perform the same actions as described herein for performance by the pump.

It is to be noted that penetrable surface 28 of housing 24 may define only a portion of the upper surface of housing 24. In such an embodiment, the upper surface of housing 24 comprises a port region which comprises penetrable surface 28.

Figure 2:
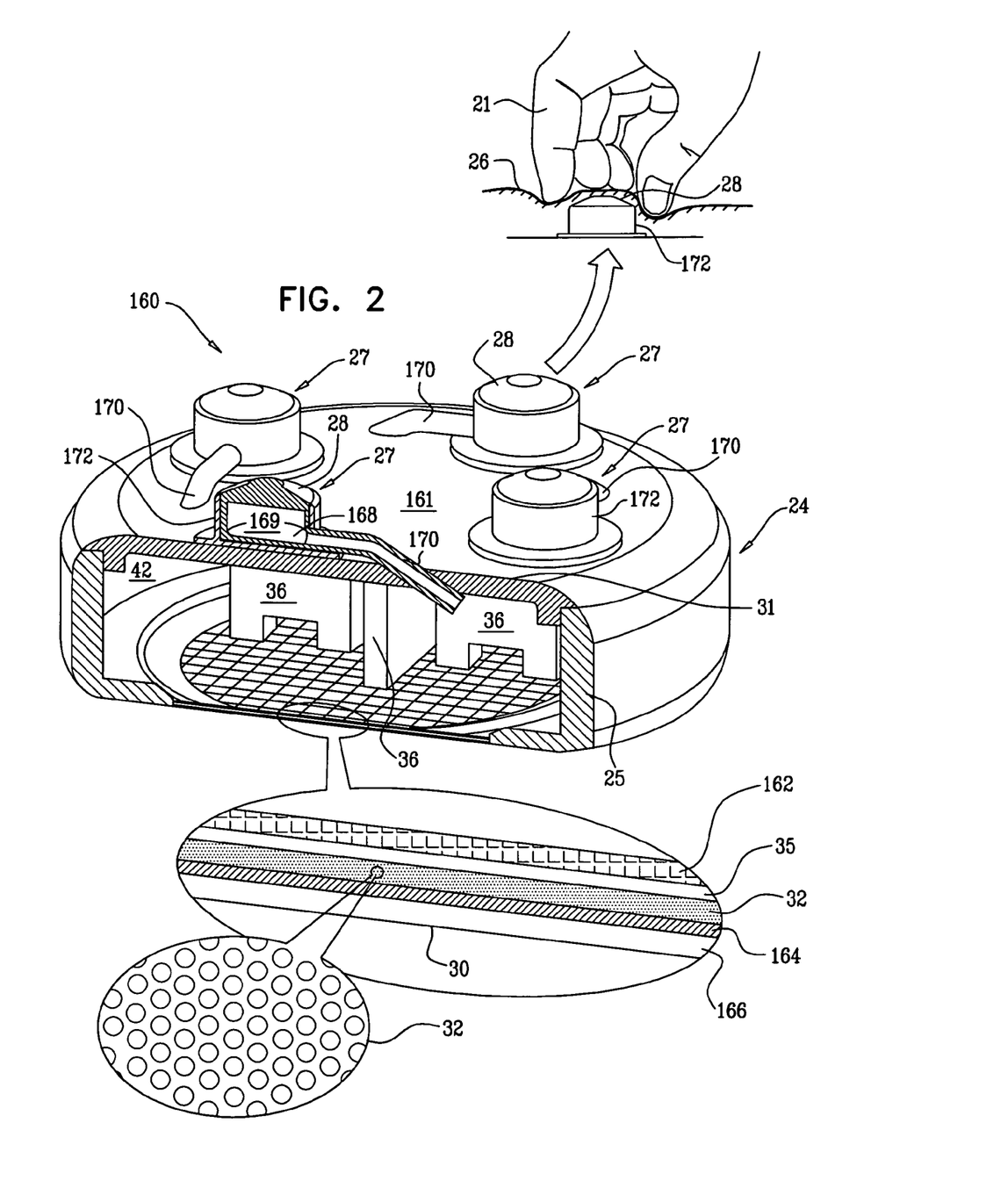
FIG. 2 is a schematic illustration of a housing coupled to a plurality of fluid-delivery ports, in accordance with an embodiment of the present invention.

FIG. 2 shows a system 160 comprising subcutaneously-implantable housing 24 coupled to a plurality of fluid-injection ports 172, in accordance with an embodiment of the present invention. Upper surface 31 comprises a rigid, impenetrable surface 161 that is supported by a plurality of mechanical supports 36. Ports 172 are disposed upon upper surface 31 and comprise a rigid, impenetrable base 168 and walls which define a port chamber 169. An upper surface of each port comprises a penetrable surface 28, which functions as oxygen delivery interface 27. A respective tube 170 facilitates transfer of oxygen from ports 172 to reservoir 42 and toward layer 32 of islets. Each tube 170 provides: (a) a first end coupled to port 172 and in fluid communication with chamber 169, (b) a body portion which crosses upper surface 31 or the side of housing 24, and (c) a second end that is in fluid communication with reservoir 42 of housing 24.

A protective grid 162 is disposed at a lower portion of housing 24. Grid 162 provides a base for supports 36. For some applications, gas-permeable membrane 35 is disposed between grid 162 and layer 32 of islets, and facilitates the transport of gases between reservoir 42 and layer 32. A second grid 164 is disposed beneath layer 32 of islets and provides support therefor. A selectively-permeable membrane 166 is typically disposed at interface 30 of housing 24 with tissue of subject 22. Selectively-permeable membrane 166 comprises a Millipore membrane having a pore size of typically, about 0.5 um, immunoisolates the transplanted cells, and facilitates transport of (a) molecules, e.g., insulin, from the cells to the body of subject 22, and (b) molecules, e.g., glucose, from the body of subject 22 to the cells in housing 24.

Typically, following implantation of housing 24 in the body of subject 22, housing 24 is primed with a suitable amount of oxygen-containing fluid. (The housing may have previously been filled with oxygen-containing fluid, as well.) Typically, subject 22 feels for at least one port 172 with his or her hand 21. Upon determining the location of the port, subject 22 transcutaneously punctures skin 26 with a first needle and subsequently penetrates penetrable surface 28 of a first port 172. In such an embodiment, the needle comprises a single-chambered needle. Typically, subject 22 then feels for a second port 172 and transcutaneously punctures surface 28 of the second port 172 with a second single-chambered needle. Impenetrable base 168 of each port 172 together with impenetrable surface 161 of housing 24 prevent passage of the needles into housing 24. The first needle is used to draw fluid from within housing 24 by lowering the pressure in chamber 169 of the first port 172. In response to reducing the pressure, fluid is drawn from reservoir 42, through tube 170, into chamber 169 of the first port 172, and finally through the first needle. In conjunction with drawing the fluid, the second needle is coupled to a source of oxygen, as described hereinabove, and facilitates the passage of oxygen-containing fluid into housing 24.

In an embodiment, oxygen-containing fluid is driven through the first needle, and oxygen-depleted fluid that had previously been in the housing is thus driven out of housing 24, to be replaced by the oxygen-containing fluid.

For some applications, a common structure holds both the first and second needles prior to and during their puncturing of the skin and surface 28 of each port.

In an embodiment, upper surface 31 of housing 24 is flexible and penetrable. In such an embodiment, only the respective bases 168 of each port prevent passage of the needle into housing 24.

Figure 3:
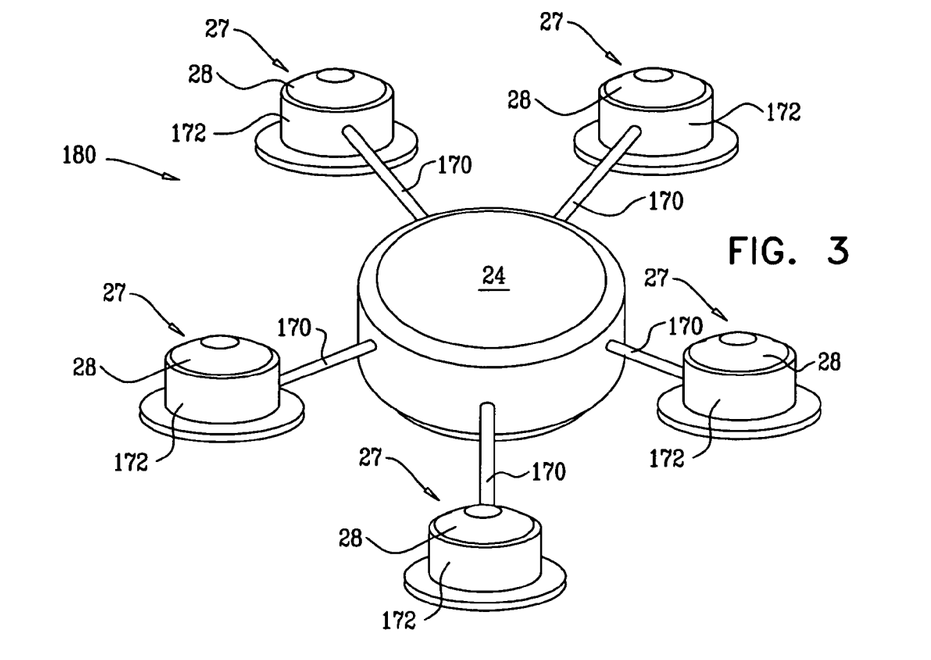
FIG. 3 is a schematic illustration of the housing coupled to a plurality of fluid delivery ports, in accordance with another embodiment of the present invention.

Reference is now made to FIG. 3, which is a schematic illustration of a system 180 similar to system 160 described hereinabove with reference to FIG. 2, with the exception that ports 172 are disposed remotely with respect to housing 24, in accordance with an embodiment of the present invention. The remote positioning of ports 172 with respect to housing 24 facilitates the delivery of fluid to housing 24 without substantially shifting the position of housing 24.

Figure 4A:
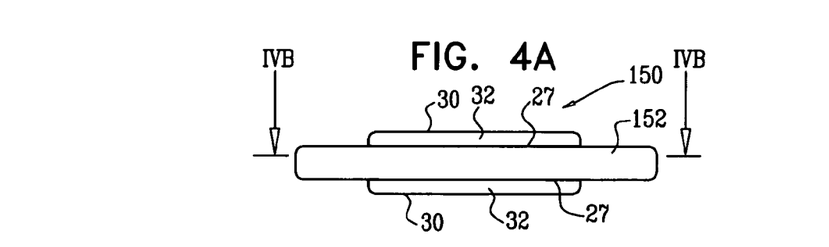
FIGS. 4A-B are schematic illustrations of an oxygen reservoir layer surrounded by two layers of functional cells, in accordance with an embodiment of the present invention.
Figure 4B:
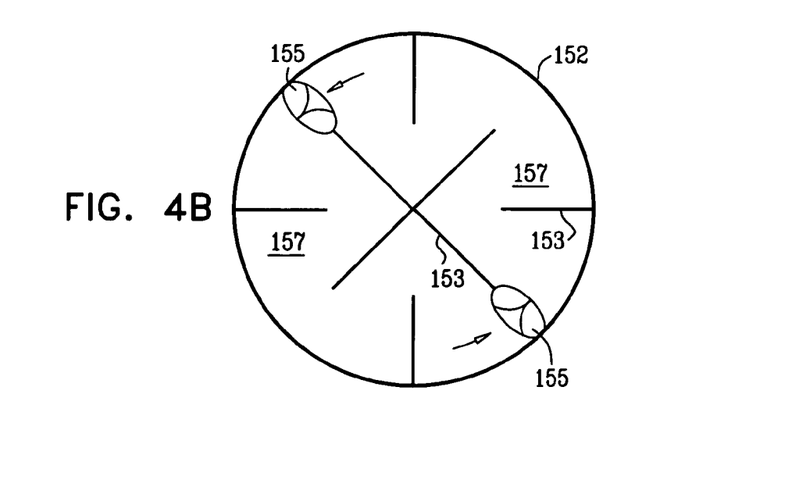

Reference is now made to FIGS. 4A-B, which are schematic illustrations of a system 150 comprising two layers 32 of functional cells which surround an oxygen reservoir layer 152, in accordance with an embodiment of the present invention. Layers 32 of functional cells comprise islets that are typically evenly distributed with respect to layers 32 in a manner as described hereinabove. Reservoir layer 152 receives and stores oxygen-containing fluid (e.g., gas comprising molecules of oxygen, or a liquid comprising oxygen carriers preloaded with oxygen). In some embodiments, layer 152 comprises a hydrogel, e.g., alginate. In some embodiments, layer 152 comprises a gas reservoir.

In some embodiments, reservoir layer 152 receives the oxygen-containing fluid from the source of oxygen via a needle (e.g., in a manner as described hereinabove with reference to FIGS. 1A-B and 2-3), or via a fluid-inlet tube (e.g., in a manner described hereinbelow with reference to FIGS. 5A-C and 6-7). It is to be noted that system 150 may be used independently or in combination with embodiments described in FIGS. 1A-B, 2-3, 5A-C, and 6-7 for supplying oxygen to reservoir layer 152. For example, reservoir layer 152 may comprise oxygen carriers and absorb oxygen from vasculature surrounding layer 152.

In some embodiments, reservoir layer 152 is pre-loaded with oxygen carriers (e.g., hemoglobin-based oxygen carriers such as chemically-modified hemoglobin, or "microbubbles" which comprise fluorocarbons such as dodecafluoropentane or perfluorodecalin). Typically, the oxygen carriers are loaded with oxygen and are supplied to reservoir layer 152 at regular intervals following the implantation of system 150.

Each layer 32 of cells has (a) an interface 30 with tissue of subject 22, and (b) an interface with reservoir layer 152 which functions as oxygen-delivery interface 27. In such an embodiment, system 150 functions as housing 24 or 124. Thus, interfaces 30 of each layer 32 with tissue of subject 22 function as oxygen delivery interfaces 27 which absorb oxygen from vasculature surrounding system 150. In such an embodiment, either surface of each layer 32 is exposed to oxygen. That is, the surface of each layer 32 at interface 30 receives oxygen from vasculature of subject 22, while the surface of each layer at the interface between layer 32 and reservoir layer 152 receives oxygen from reservoir layer 152.

It is to be noted that although only two layers 32 of cells are shown, any suitable number of layers of cells may be coupled to reservoir layer 152. It is to be further noted that layers 32 are shown as being flat by way of illustration and not limitation. For example, layer 32 may be shaped to define various thicknesses along the slab. In some embodiments, layer 32 is thicker at the center and thinner along the edges.

In some embodiments, system 150 is integrated within housing 24 (described hereinabove with reference to FIGS. 1A-B and 2-3, and as described hereinbelow with reference to FIGS. 5A-C) or with housing 124 as described hereinbelow with reference to FIGS. 6-7. For embodiments in which system 150 is integrated within housings 24 or 124, interface 30 of a first layer 32 is in contact with tissue of subject 22, while interface 30 of a second layer 32 is in contact with reservoir 42 of housing 24. In such an embodiment, interface 30 that is in contact with tissue of subject 22 functions as oxygen delivery interface 27, because interface 30 facilitates transport of oxygen to the islets in layer 32 from surrounding vasculature of subject 22.

Typically, layer 152 has a diameter of around 10 cm and a thickness of between 1 mm and 3 cm, e.g., around 2 mm, while each layer 32 of islets has a smaller diameter of around 8 cm and a thickness of less than 1 mm. The larger diameter of reservoir layer 152 with respect to layers 32 of islets create portions of layer 152 that are exposed to tissue of subject 22. These portions create a greater surface area for reservoir layer to absorb oxygen from surrounding vasculature of subject 22. For applications in which reservoir layer comprises the oxygen carriers, the oxygen carriers absorb the excess oxygen in layer 152.

FIG. 4B shows a cross-section of oxygen reservoir layer 152. Layer 152 comprises walls 153 comprising a flexible material, e.g., silicone. Walls 153 define a series of channels 157 for directed transport of oxygen through layer 152. Typically, layer 152 comprises unidirectional valves, e.g., mechanical or electromechanical valves, which facilitate directional transport of the oxygen-containing fluids within channels 157. Typically, the fluid transport is induced passively in response to increased pressure within layer 152 in response to an increase of oxygen in layer 152. For some applications, system 150 is implanted in the ribcage of subject 22. In such an embodiment, the fluid within layer 152 is circulated in response to movements of layer 152 responsively to the movements of the ribcage during respiration.

It is to be noted that the number and spatial configurations of walls 153 and valves 155 are shown by way of illustration and not limitation, and that layer 152 may comprise any suitable-number of valves and walls which direct the flow of oxygen in any suitable direction. Walls 153 may be oriented in a manner which provides channels 157 shaped differently than as illustrated.

Figure 5A:
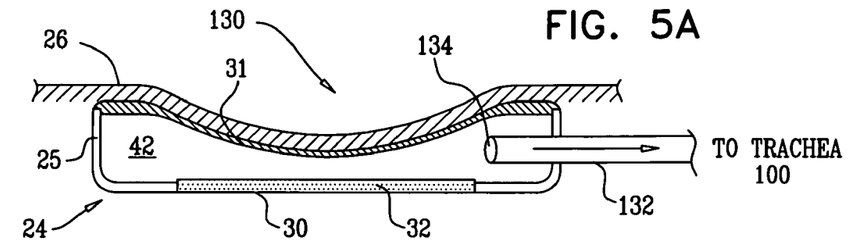
FIGS. 5A-C are schematic illustrations of a housing indirectly coupled to a trachea of a subject, in accordance with an embodiment of the present invention.
Figure 5B:
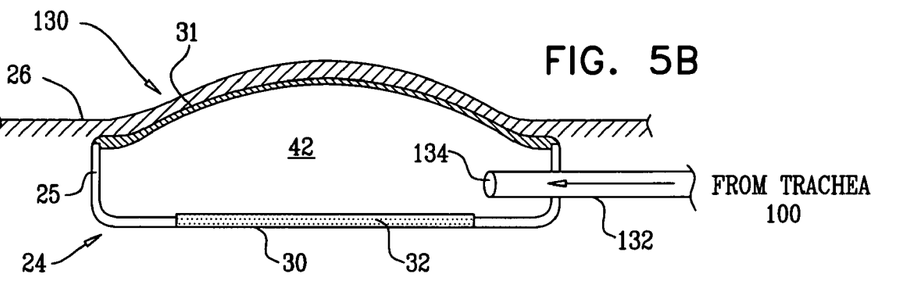
Figure 5C:
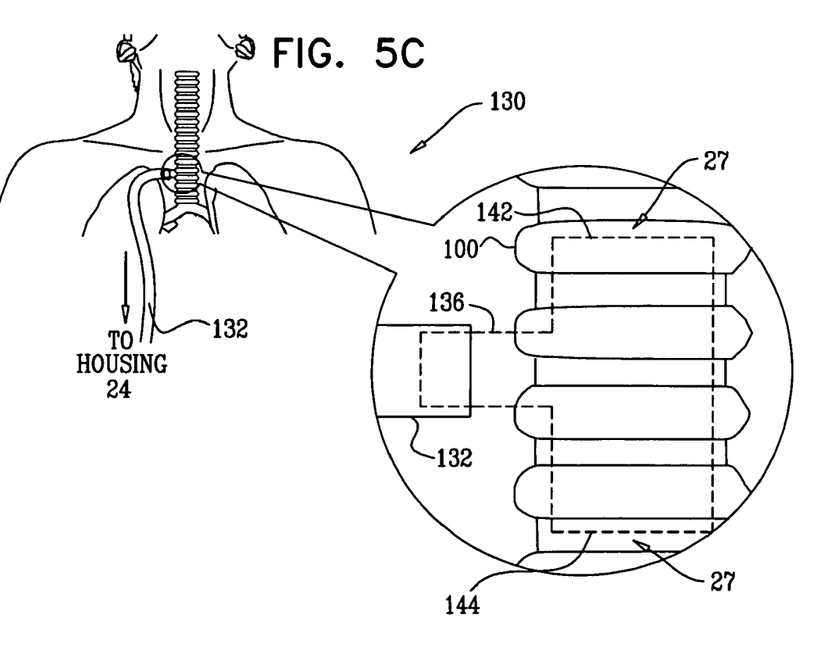

FIGS. 5A-C show a system 130 comprising subcutaneously-implantable housing 24 which is configured to receive oxygen from a trachea 100 of subject 22, in accordance with an embodiment of the present invention. Housing 24 is typically disposed remotely from trachea 100, and is coupled thereto via an air-transport tube 132. Typically, housing 24 is disposed in the abdomen of subject 22. For some applications, housing 24 is disposed in the ribcage of subject 22.

Transport tube 132 typically comprises silicone and is coupled at a first end 134 thereof to housing 24 and is thereby in fluid communication with reservoir 42 (as shown in FIGS. 5A-B). A second end of tube 132 is coupled to a base of a "T"-shaped tracheal mount 136 (as shown in FIG. 5C). Respective ends 142 and 144 of tracheal mount 136 are disposed within trachea 100 of subject 22. Ends 142 and 144 define ends of a vertical lumen of tracheal mount 136 and function as a shunt to channel air toward tube 132 such that the channeled air eventually reaches housing 24. As such, tracheal mount 136 functions as oxygen delivery interface 27.

Housing 24 comprises scaffold 25 which supports upper surface 31. In the embodiment shown in FIGS. 5A-B, upper surface 31 is flexible, and depressible. Housing 24 is subcutaneously implanted such that surface 31 is depressible by subject 22 when force is applied to surface 31 in response to subject 22 pressing on the skin above surface 31. As shown in FIG. 5A, responsively to the pressing, air is forced out of reservoir 42 (as indicated by the arrow), through tube 132, and is emptied into trachea 100 via tracheal mount 136.

FIG. 5B shows the release of surface 31 following the pressing thereof. Since surface 31 is resilient, surface 31 returns to its original shape, as shown, which creates lower pressure in housing 24 and forces oxygen-containing air from trachea 100 into reservoir 42 of housing 24 (as indicated by the arrow). Thus, system 130 functions as a pumping mechanism which enables subject 22 to pump oxygen-containing air into housing 24 from trachea 100.

Figures 6, 7:
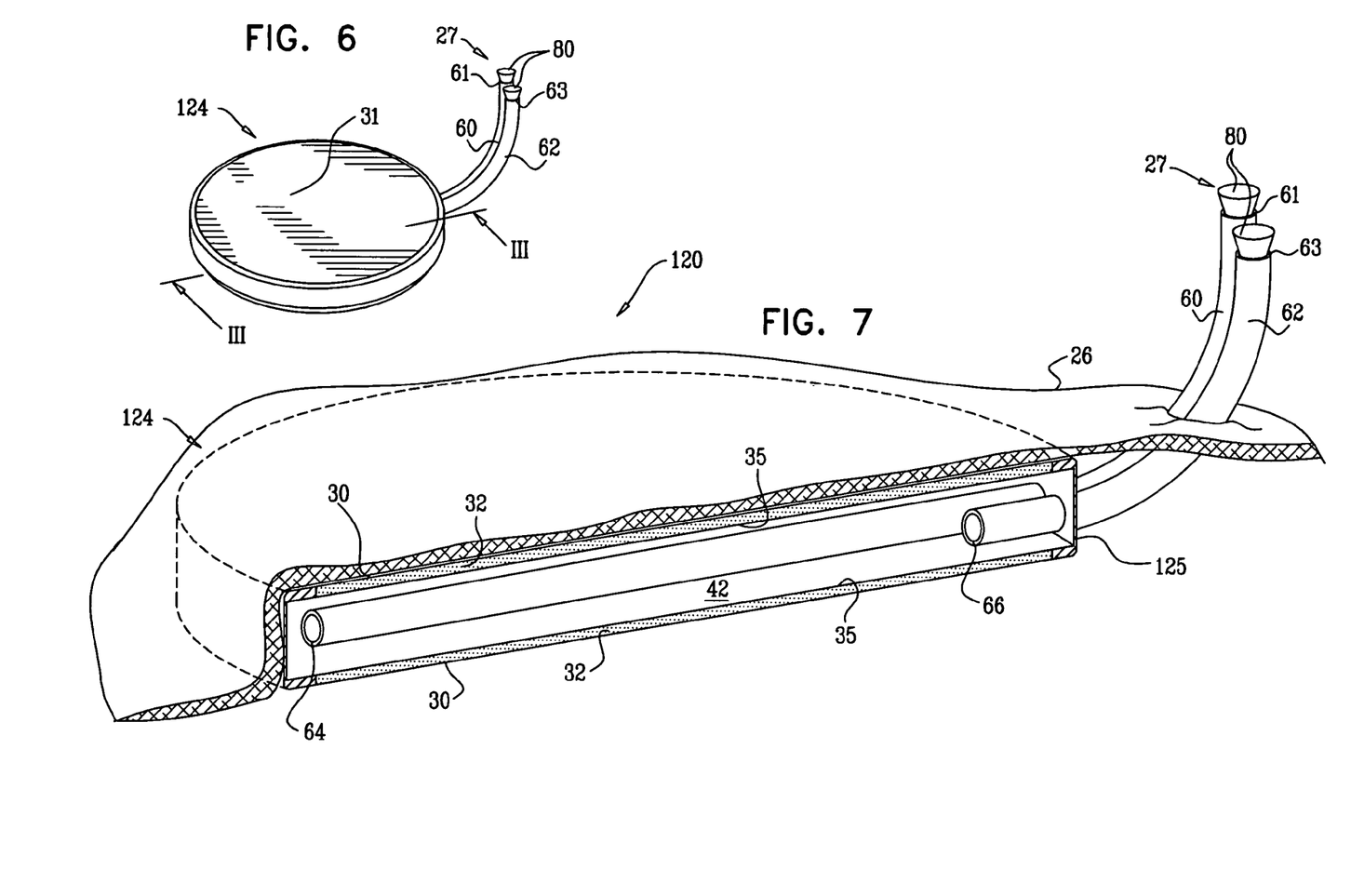
FIGS. 6 and 7 are schematic illustrations of a housing coupled to a fluid inlet tube and a fluid outlet tube and housing functional cells, in accordance with an embodiment of the present invention.

Reference is now made to FIGS. 6-7, which are schematic illustrations of a system 120 comprising a subcutaneously-implantable housing 124 in fluid communication with and coupled to a transcutaneous fluid inlet tube 60 and a transcutaneous fluid outlet tube 62, in accordance with an embodiment of the present invention. Respective first ends 64 and 66 of tubes 60 and 62 are disposed within housing 124, while respective second ends 61 and 63 of tubes 60 and 62 are disposed externally to skin 26 of the subject. End 61 of fluid inlet tube 60 serves as oxygen delivery interface 27. Respective plugs 80 are coupled to each end 61 and 63 of tubes 60 and 62, respectively, and function to reversibly seal tubes 60 and 62 when the tubes are not in use.

It is to be noted that tubes 60 and 62 are disposed at the same side of housing 124 by way of illustration and not limitation. For example, tubes 60 and 62 may be disposed at opposite sides of housing 124.

Housing 124 comprises a scaffold 125, as described hereinabove with respect to scaffold 25 with reference to FIGS. 1A-B. Scaffold 125 surrounds reservoir 42 and supports one or more layers 32 of functional cells. Typically, one layer 32 is disposed at an upper surface of housing 124 and another layer 32 is disposed at a lower surface of housing 124. A respective gas-permeable membrane 35 is disposed between each layer 32 of functional cells and reservoir 42. For embodiments in which housing 124 holds 400,000 islets, each layer 32 of functional cells comprises 200,000 islets. For embodiments in which housing 124 holds 40,000 islets, each layer 32 of functional cells comprises 20,000 islets.

A source of oxygen (not shown), e.g., a vessel such as a syringe or a pre-filled cartridge, comprising a source of oxygen-containing fluid is coupled to tube 61 at oxygen delivery interface 27. The source of oxygen supplies the fluid to housing 124 via fluid inlet tube 61. In some embodiments, the source of oxygen comprises air or another mixture of gases. Alternatively, the source of oxygen comprises pure oxygen. In some embodiments, the source of oxygen comprises a liquid comprising oxygen carriers, as described hereinabove. In conjunction with supplying oxygen to housing 124, fluid having a low oxygen content is expelled from within housing 124 via fluid outlet tube 62. In some embodiments, the fluid is passively expelled from housing 124 in response to pressure introduced within housing 124 due to the injection of the fluid having a high oxygen content. Alternatively or additionally, a source of suction is coupled at end 63 of tube 62 and actively draws fluid from within housing 124.

As shown, first end 64 of tube 60 is disposed within housing 124 at a substantial distance from end 66 of tube 62 (e.g., greater than 50% of the longest dimension of housing 124, or greater than 75% of the longest dimension of housing 124). Such a configuration allows the transport of fluid from the source of oxygen to housing 124 via fluid inlet tube 60, while minimizing the possibility of immediate withdrawing of the transported fluid through fluid outlet tube 62.

In some embodiments of the present invention, a moisture-absorbing element (not shown) is disposed in housing 124 in a vicinity of end 66 of fluid outlet tube 62 or elsewhere in the housing. The moisture absorbing element helps facilitate a balance of moisture in housing 124. Housing 24 (described hereinabove with reference to FIGS. 1A-B) may also comprise the moisture-absorbing element.

In some embodiments, reservoir 42 of housing 24 comprises foam, e.g., an open-cell silicone foam, to maintain a distance between and support layers 32 of functional cells (in a manner similar to supports 36 of housing 24 described hereinabove with reference to FIGS. 1A-B). Alternatively or additionally, supports 36 are integrated into housing 124.

Reference is now made to FIGS. 1A-B, and 2-7. Following the replenishing of housings 24 and 124 with fluid having a high oxygen content, the source of oxygen is detached from oxygen delivery interface 27. At regular intervals, e.g., once every 1-7 days or once every 7-35 days, the source of oxygen is coupled by the user to interface 27 and supplies oxygen to housing 24 and 124.

Reference is now made to FIGS. 3, 4, 5A-C, and 6-7. Reservoir layer 152 of system 150 (described hereinabove with reference to FIG. 4) may be used in combination with any of oxygen delivery interfaces 27 described hereinabove with reference to FIGS. 3, 5A-C, and 6-7. That is, in some embodiments, reservoir layer 152 is coupled to tubes 170 and is loaded with oxygen via ports 172 that are coupled to tubes 170, in a manner as described hereinabove with reference to FIG. 3. For some applications, reservoir layer 152 is coupled to tube 132 which receives oxygen-containing gas from trachea 100, in a manner as described hereinabove with reference to FIGS. 5A-C. In an embodiment, reservoir layer 152 is coupled to transcutaneous tubes 60 and 62 and receives oxygen-containing fluid from fluid-inlet tube 60, in a manner as described hereinabove with reference to FIGS. 6-7.

Typically, layers 32 and 152 of system 150 are flexible and are configured for implantation in a vicinity of a ribcage of subject 22. In such an embodiment, reservoir layer 152 moves and contorts responsively to the natural movements of the ribcage of subject 22. Consequently, the oxygen-containing fluid disposed within reservoir layer 152 is forcefully moved therein such that the fluid is circulated within layer 152 and toward the surrounding layers 32 of islets. In some embodiments, layer 152 comprises a liquid or gel, e.g., alginate. For embodiments in which layer 152 comprises a gel, layer 152 may be shaped to define channels and or valves which create a path for directed transport of the oxygen-containing fluid within layer 152.

Reference is yet again made to FIGS. 1A-B and 2-7. Apparatus described herein may comprise layers 32 of functional cells independently of or in combination with grids 162 and 164 and/or membranes 35 and 166, as described hereinabove with reference to FIG. 2.

Reference is yet again made to FIGS. 1A-B and 2-7. It is to be noted that the scope of the present invention includes the use of apparatus described herein for implanting functional cells other than pancreatic islets of Langerhans, e.g., cells of the thyroid gland, cells of the adrenal gland, hepatic cells, and cells that are genetically modified so as to secrete a therapeutic protein.

Reference is additionally made to FIGS. 1A-B and 2-7. In some embodiments, housings 24 and 124 are coupled to a subcutaneously-implantable source of oxygen, or reservoir. The implantable oxygen source is coupled to housings 24 and 124 via at least one tube. For some applications, oxygen is passed from the oxygen source to housings 24 and 124 in an at least somewhat regulated manner. For example, the tube connecting the implanted oxygen source to housing 24 or 124 may comprise a unidirectional valve (e.g., a mechanical or electromechanical valve) which helps regulate a rate of transport of fluid into housing 24 or 124. Typically, the implanted source of oxygen comprises between 100 ml and 300 ml of fluid at a pressure of up to 1000 atm (e.g., 1-10 atm, 10-100 atm, or 100-1000 atm).

The scope of the present invention includes embodiments described in the following patents and patent applications, which are incorporated herein by reference. In an embodiment, techniques and apparatus described in one or more of the following patents and patent applications are combined with techniques and apparatus described herein:

PCT Patent Publication WO 01/050983, filed Jan. 12, 2001, entitled, "Implantable device";

U.S. patent application Ser. No. 10/466,069, filed Mar. 12, 2004, entitled, "Implantable device";

US Patent Application Publication 2005/0136092, filed Nov. 30, 2004, entitled, "Implantable device";

PCT Patent Publication WO 06/059322, filed Nov. 27, 2005, entitled, "Implantable device";

U.S. Provisional Patent Application 60/860,632, filed Nov. 22, 2006, entitled, "Protecting algae from body fluids";

U.S. Provisional Patent Application 60/861,592, filed Nov. 28, 2006, entitled, "Oxygen supply for cell transplant and vascularization";

PCT Patent Application PCT/IL07/001471, filed Nov. 28, 2007, entitled, "Oxygen supply for cell transplant and vascularization";

U.S. Provisional Patent Application 60/993,052, filed Sep. 7, 2007, entitled, "Air gap for supporting cells";

PCT Patent Application PCT/IL07/001447, filed Nov. 22, 2007, entitled, "Protecting algae from body fluids";

U.S. patent application Ser. No. 12/064,946, filed Feb. 26, 2008, entitled, "Oxygen supply for cell transplant and vascularization";

PCT Patent Application PCT/IL08/001204, filed Sep. 7, 2008, entitled, "Air gap for supporting cells"; and U.S. Provisional Patent Application 61/192,412, filed Sep. 17, 2008, entitled, "Optimization of alginate encapsulation of islets for transplantation."

For some applications, techniques described herein are practiced in combination with techniques described in one or more of the references cited in the Background section of the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   a housing, configured for implantation in a body of a subject;
   functional cells, coupled to the housing;
   a source of oxygen disposed outside of the housing and configured to supply gaseous oxygen to the functional cells;
   an oxygen delivery interface at an outer surface of the housing, the oxygen delivery interface:
      comprising at least in part a penetrable surface for receiving a needle therethrough, and
      configured to receive oxygen from the source of oxygen, and to facilitate passage of the oxygen to the functional cells, while the housing is disposed within the body of the subject; and
   an oxygen reservoir coupled to the housing and in fluid communication with the functional cells, the oxygen reservoir being configured to store the gaseous oxygen from the source of oxygen.

2. The apparatus according to claim 1, wherein the functional cells comprise cells disposed in pancreatic islets.

3. The apparatus according to claim 1, wherein the source of oxygen comprises a plurality of gases.

4. The apparatus according to claim 1, wherein the oxygen delivery interface is reversibly couplable to the source of oxygen.

5. The apparatus according to claim 1, wherein the housing is configured to have a volume sufficient to sustain the functional cells for a period of between 12 hours and 2 weeks.

6. The apparatus according to claim 1, wherein the housing is shaped to provide a plurality of projections which project into tissue of the subject, the projections being configured to absorb oxygen from vasculature of the subject.

7. The apparatus according to claim 1, wherein the functional cells are disposed in at least one layer of hydrogel configured to immunoisolate the cells from the body of the subject.

8. The apparatus according to claim 7, wherein the functional cells are disposed in at least first and second layers of hydrogel, the first and second layers being disposed on either side of the oxygen reservoir.

9. The apparatus according to claim 8, wherein the oxygen reservoir has a longest dimension that is longer than a longest dimension of either of the first and second layers of the functional cells, and wherein the oxygen reservoir provides surface area for absorbing oxygen from surrounding vasculature of the subject.

10. The apparatus according to claim 8, wherein the oxygen reservoir is shaped to provide a series of channels which facilitate directed transport of fluids within the oxygen reservoir.

11. The apparatus according to claim 10, wherein the oxygen reservoir comprises at least one valve configured to facilitate directed transport of fluids within the oxygen reservoir.

12. The apparatus according to claim 8, wherein the housing is configured to be implanted in a vicinity of a ribcage of the subject, and wherein the housing is configured to circulate the oxygen in the reservoir in response to movements of the housing responsively to movements of the ribcage of the subject.

13. The apparatus according to claim 12, wherein the oxygen reservoir comprises a hydrogel shaped to define a channel configured to facilitate directed transport of oxygen within the reservoir.

14. The apparatus according to claim 1, wherein the oxygen reservoir is disposed adjacently to the oxygen delivery interface and is couplable to and receives oxygen from the source of oxygen.

15. The apparatus according to claim 14, wherein the oxygen reservoir comprises oxygen carriers.

16. The apparatus according to claim 1, wherein:
   during a first time, the interface is configured to facilitate:
      coupling of the source of oxygen to the housing,
      supplying of oxygen from the source of oxygen to the cells coupled to the housing, and
      decoupling of the source of oxygen from the interface following the supplying of oxygen, and
   at a second time, the interface is configured to facilitate:
      coupling of the source of oxygen to the housing,
      supplying of oxygen from the source of oxygen to the cells coupled to the housing, and
      decoupling of the source of oxygen from the interface following the supplying of oxygen.

17. The apparatus according to claim 16, wherein:
   the apparatus further comprises the needle,
   the needle is configured for transcutaneously penetrating the penetrable surface,
   the housing is indirectly couplable to the source of oxygen via the needle, and
   the needle facilitates supplying of oxygen to the cells from the source of oxygen.

18. The apparatus according to claim 17, wherein the housing is shaped to define an upper surface, and wherein the penetrable surface comprises the upper surface of the housing.

19. The apparatus according to claim 17, wherein the oxygen delivery interface comprises at least one oxygen-delivery port having an upper surface thereof and a tube coupled at a first end thereof to the port and at a second end thereof to the housing, and wherein the upper surface of the port comprises the penetrable surface that is penetrable by the needle.

20. The apparatus according to claim 19, wherein the port is coupled to an upper surface of the housing.

21. The apparatus according to claim 19, wherein the port is disposed remotely from the housing.

22. The apparatus according to claim 1, wherein the oxygen reservoir is configured to store the gaseous oxygen at a pressure of at least 1 atm.

23. The apparatus according to claim 1, wherein a volume of the reservoir is between 100 ml and 300 ml.

24. The apparatus according to claim 1, wherein the oxygen reservoir comprises oxygen carriers configured to absorb excess oxygen disposed in the oxygen reservoir.

25. The apparatus according to claim 1, further comprising a gas-permeable membrane disposed between the reservoir and the functional cells.

26. The apparatus according to claim 1, wherein:

the apparatus comprises the needle, the needle is couplable to the source of oxygen and is configured for transcutaneous penetration of the penetrable surface, the needle comprises at least a first chamber and a second chamber, the first chamber is configured to facilitate delivery of oxygen from the source of oxygen to the functional cells coupled to the housing, and the second chamber is configured to facilitate passage of fluid from within the housing to outside the body of the subject.

27. The apparatus according to claim 26, wherein the second chamber is configured to facilitate passive passage of the fluid from within the housing, in conjunction with the supplying of oxygen to the housing by the first chamber.

* * * * *